(12) United States Patent
Saraf

(10) Patent No.: US 7,001,477 B2
(45) Date of Patent: Feb. 21, 2006

(54) CUTTING METHOD AND APPARATUS HAVING AN AFFIXED KNIFE

(75) Inventor: Moshe Saraf, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 149 days.

(21) Appl. No.: 10/726,107

(22) Filed: Dec. 2, 2003

(65) Prior Publication Data

US 2005/0115665 A1  Jun. 2, 2005

(51) Int. Cl.
*B32B 31/00* (2006.01)

(52) U.S. Cl. .................. 156/251; 156/515; 156/518; 83/591; 83/674

(58) Field of Classification Search ............... 156/251, 156/515, 517, 518; 83/863, 884, 591, 674
See application file for complete search history.

(56) References Cited

U.S. PATENT DOCUMENTS

| | | | |
|---|---|---|---|
| 3,616,095 A * | 10/1971 | Membrino | 156/582 |
| 3,801,409 A | 4/1974 | Plate et al. | |
| 3,901,759 A | 8/1975 | Highfield et al. | |
| 3,957,569 A | 5/1976 | Freitag | |
| 4,255,225 A | 3/1981 | Evers | |
| 4,308,776 A | 1/1982 | Gillespie et al. | |
| 4,785,697 A | 11/1988 | Gherardi | |
| 5,224,408 A * | 7/1993 | Steidinger | 83/674 |
| 5,226,344 A * | 7/1993 | Rosemann | 83/674 |
| 5,253,561 A * | 10/1993 | Wynn | 83/674 |
| 5,417,132 A * | 5/1995 | Cox et al. | 83/116 |

FOREIGN PATENT DOCUMENTS

EP          0 841 133 B1    10/2002

* cited by examiner

*Primary Examiner*—Mark A. Osele
(74) *Attorney, Agent, or Firm*—Paul Yee

(57) ABSTRACT

A cutting method and apparatus (20) includes a rotary cutter (28) having an axial-direction (22), a radial-direction (24) and a circumferential-direction (26). The rotary cutter (28) includes a rotary shaft member (30) having an outer peripheral surface (32), and at least one knife member (36) joined to the shaft member (30). At least a portion of the knife member (36) extends axially along the shaft member (30) and extends radially outward from the shaft member. In a particular feature, at least one peripheral bearing member (40) and desirably, at least a cooperating pair of peripheral bearing members (40) can be joined to the rotary shaft member (30). At least an operative portion of each peripheral bearing member (40) extends radially outward from the shaft member (30) and extends circumferentially about the shaft member.

23 Claims, 12 Drawing Sheets

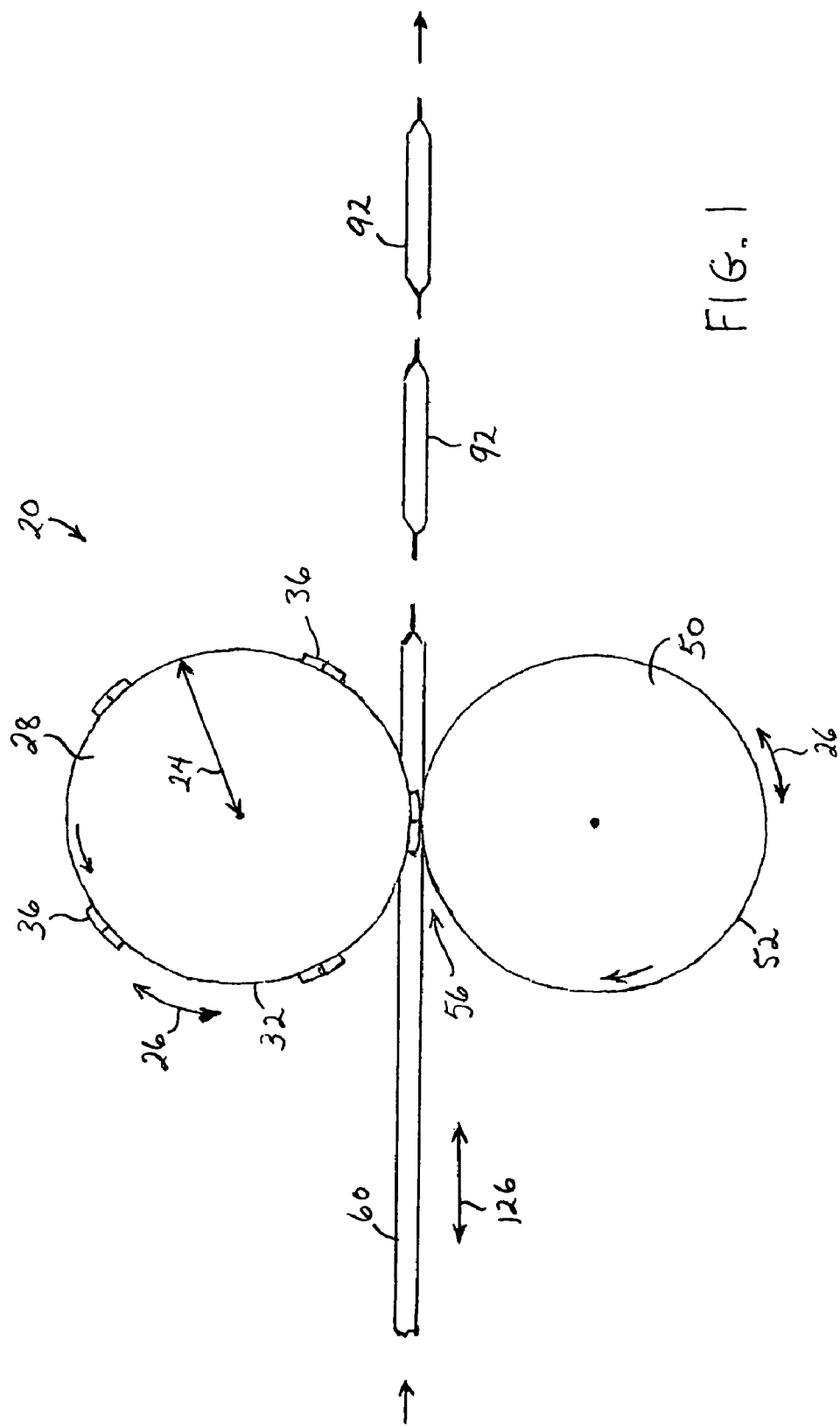

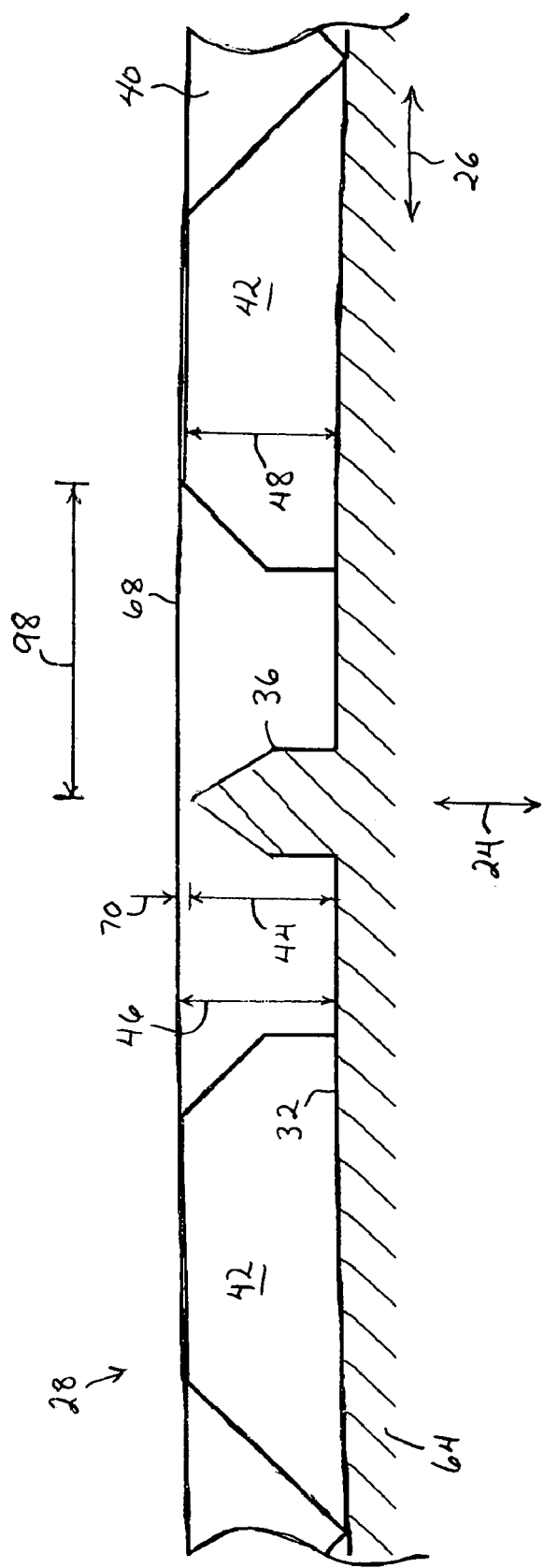

CUTTING METHOD AND APPARATUS HAVING AN AFFIXED KNIFE

FIELD OF THE INVENTION

The present invention relates to a cutting system. More particularly, the present invention pertains to a rotary cutting system having a knife member.

BACKGROUND OF THE INVENTION

Conventional rotary cutting systems has been employed to cut product webs employed to produce personal care absorbent articles. Typical cutting systems have included rotary knife rolls and cooperating, rotary anvil rolls. The knife rolls have been configured to provide an array of cutting dies to provide cutting lines arranged with selected shapes. Other conventional cutting systems have included bonding components for providing crimps or other construction bonds. In particular systems, the construction bonds have been located adjacent the regions of product webs where the product webs have been cut.

In conventional cutting systems the cutting knives have been susceptible to excessive wear and have required excessive maintenance. To address these problems, conventional cutting systems have employed knives which can selectively move and retract away from a cutting surface to reduce the wear and degradation of the cutting edges of the knives. The retractable or otherwise moveable knife systems, however, have been susceptible to binding or clogging caused by troublesome accumulations of stray particles of cut material.

To help maintain the reliability of the bonding and cutting of the product web, conventional manufacturing systems have employed separate equipment modules to perform the bonding and cutting operations. With such conventional systems, the bonding operation has typically been performed prior to the cutting operation. The separate processing modules, however, have contributed to increased complexity and cost, and have required increased amounts of space.

It has been desirable to provide the cutting and bonding operations in a single, combined equipment module. Conventional systems and techniques for providing the combined cutting and bonding operations, however, have not been sufficiently reliable. The bonding and cutting of the product web have not been sufficiently consistent, particularly when conducted at high manufacturing speeds. Additionally, the employed cutting knives have been susceptible to excessive wear, and the equipment has required excessive maintenance.

As a result, there has been a continuing need for a more compact method and apparatus that can provide a combined bonding and cutting operation with increased reliability, increased efficiency and lower cost. Additionally, there has been a continuing need for an improved method and apparatus for reliably cutting a product web at high speeds while avoiding excessive wear of the cutting knives and avoiding excessive maintenance costs.

BRIEF DESCRIPTION OF THE INVENTION

Generally stated, an apparatus aspect of the present invention can include a rotary cutter having an axial-direction, a radial-direction and a circumferential-direction. The rotary cutter has an outer peripheral surface and includes a rotary shaft member. At least one knife member is joined to the shaft member. At least a portion of the knife member can extends axially along the shaft member and can extend radially outward from the shaft member. In particular feature, at least one peripheral bearing member can be joined to the rotary shaft member, and at least an operative portion of the peripheral bearing member can extend radially outward from the shaft member and extend circumferentially about the shaft member.

In a method aspect, the present invention can provide a cutting process which can include rotating a rotary cutter which has an outer peripheral surface and includes a rotary shaft member. At least one knife member has been joined to the shaft member. At least a portion of the knife member can extend axially along the shaft member, and can extend radially outward from the shaft member. In a particular feature, at least one peripheral bearing member has been joined to the rotary shaft member. At least a portion of the peripheral bearing member can extend radially outward from the shaft member, and can extend circumferentially around the shaft member.

In a particular aspect, at least a pair of axially spaced-apart bearing members can be joined to the rotary shaft member. In another aspect of the method and apparatus, the knife member can be substantially fixedly attached to the rotary shaft member. In further aspects, the cutting method and apparatus can further include at least one bonding member which is joined to the rotary shaft member. The bonding member can be located proximate the knife member and positioned circumferentially adjacent the knife member.

With its various aspects and configurations, the distinctive apparatus and method of the present invention can more efficiently and more effectively cut a product web. The apparatus and method can more reliably maintain the effectiveness of the cutting knives, and can more efficiently conduct the cutting operation at lower cost. The cutting operation can more efficiently be coordinated and/or combined with other manufacturing operations, such as a bonding operation. In particular aspects, the bonding operation can provide a crimping or sealing of the product web. As a result, the method and apparatus of the present invention can help eliminate the need for additional processing equipment, and can help reduce manufacturing costs.

BRIEF DESCRIPTION OF THE DRAWINGS

FIG. 1 shows a schematic elevational view of a representative method and apparatus for selectively cutting an appointed product web.

FIG. 5B shows an enlarged cross-sectional view of a representative cutter insert member that has bonding members which extends radially beyond their cooperating cutter knife.

DETAILED DESCRIPTION OF THE INVENTION

Figure 1A:
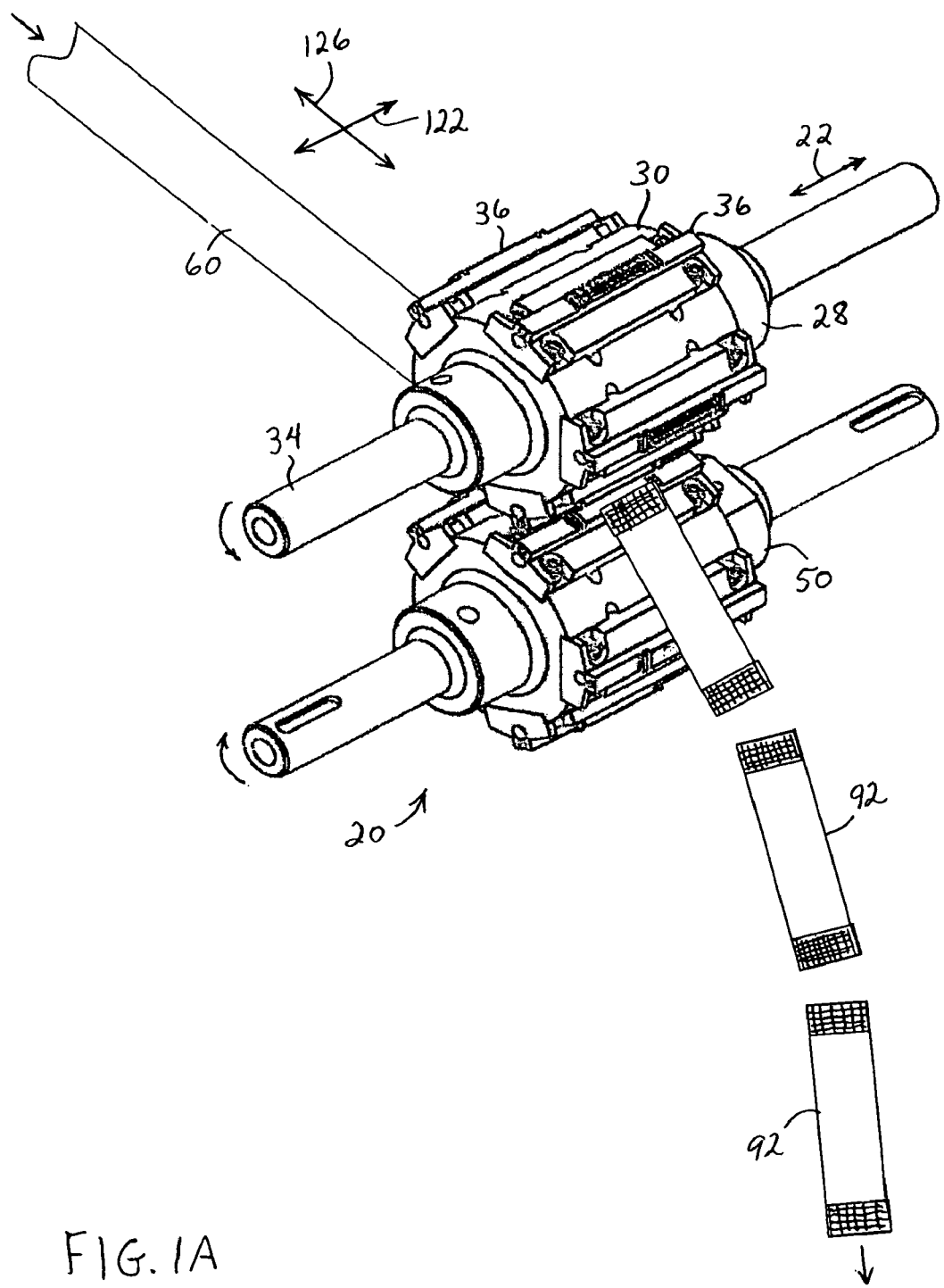
FIG. 1A shows a schematic perspective view of a representative method and apparatus selectively cutting an appointed product web.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid distribution layers, barrier layers, and the like, as well as combinations thereof.

With reference to FIGS. 1 and 1A, the method and apparatus of the invention can have an appointed machine-direction 126 which extends longitudinally, and an appointed lateral cross-direction 122 which extends transversely. For the purposes of the present disclosure, the machine-direction 126 is the direction along which a particular component or material is transported length-wise along and through a particular, local position of the apparatus and method. The cross-direction 122 lies generally within the plane of the material being transported through the method and apparatus, and is aligned perpendicular to the local machine-direction 126. Accordingly, with reference to the arrangement representatively shown in FIG. 1, the cross-direction 122 extends perpendicular to the plane of the sheet of the drawing.

With reference to FIG. 1 and FIGS. 3 through 5B, the cutting apparatus 20 can include a rotary cutter 28 having an axial-direction 22, a radial-direction 24 and a circumferential-direction 26. The rotary cutter 28 has an outer peripheral surface 32 and includes a rotary shaft member 30. At least one knife member 36 is operatively joined to the shaft member 30. At least a portion of the knife member 36 can extend axially along the shaft member 30 and can extend radially outward from the shaft member. In particular aspects, at least one and desirably at least a pair of axially spaced-apart, peripheral bearing members 40 are joined to the rotary shaft member 30. Additionally, at least an operative portion of each peripheral bearing member 40 extends radially outward from the shaft member 30 and extends circumferentially about the shaft member.

The cutting method can include rotating a rotary cutter 28 which has provided an outer peripheral surface 32 and has included a rotary shaft member 30. At least one knife member 36 has been joined to the shaft member 30. At least a portion of the knife member 36 can extend axially along the shaft member 30, and can extend radially outward from the shaft member. In particular aspects, at least one and desirably at least a cooperating pair of axially spaced-apart peripheral bearing members 40 have been joined to the rotary shaft member 30. At least a portion of each peripheral bearing member 40 can extend radially outward from the shaft member 30, and can extend circumferentially around the shaft member.

In another aspect, the knife member 36 can be substantially fixedly attached to the rotary shaft member 30. The cutting method and apparatus can further include at least one crimping or other bonding member 42. The bonding member can be operatively joined to the rotary shaft member 30, and can be located proximate the knife member 36 and positioned circumferentially adjacent the knife member 36.

In a particular aspect of the invention, a bonding mechanism can be operatively combined with the cutting method and apparatus. In still other aspects, the bonding mechanism can include a crimping mechanism and a sealing mechanism. Accordingly, the present invention, the cutting method and apparatus can be configured to operatively separate the product web 60 into a plurality of individual product articles 92.

The method and apparatus can further include an anvil 50 which has been configured to cooperate with the rotary cutter 28 to provide an operative cutting region 56 which is located in a region between the rotary cutter 28 and the anvil 50. The anvil 50 can be provided by any operative component structure or mechanism. The anvil 50 can have a substantially smooth anvil surface, or may have a patterned anvil surface. For example, the cooperating anvil surface can include an array anvil elements or members that cooperatively match a pattern of cutting elements or members that are located on the rotary cutter 28. As representatively shown, the anvil 50 can be a rotary anvil which is operatively rotatable about an anvil axis of rotation and positioned operatively adjacent the rotary cutter 28. The anvil can be configured to counter-rotate relative to the rotary cutter 28, and the cutting region 56 can be provided in a nip region that is positioned between the rotary cutter 28 and the counter-rotating anvil 50. Accordingly, the product web 60 can operatively move at a selected cutting speed through the nip region 56. Conventional rotary anvils are well known and are available from commercial vendors.

By incorporating its various aspects, features and configurations, alone or in combination, the apparatus and method of the present invention can more efficiently and more effectively cut a product web. The apparatus and method can more reliably maintain the effectiveness of the cutting knives, and can more efficiently conduct the cutting operation at lower cost. The cutting operation can more efficiently be coordinated and/or combined with other manufacturing operations, such as a bonding operation. In particular aspects, the bonding operation can provide a crimping or sealing of the product web. As a result, the method and apparatus of the present invention can help eliminate the need for additional processing equipment, and can help reduce manufacturing costs.

Figure 2:
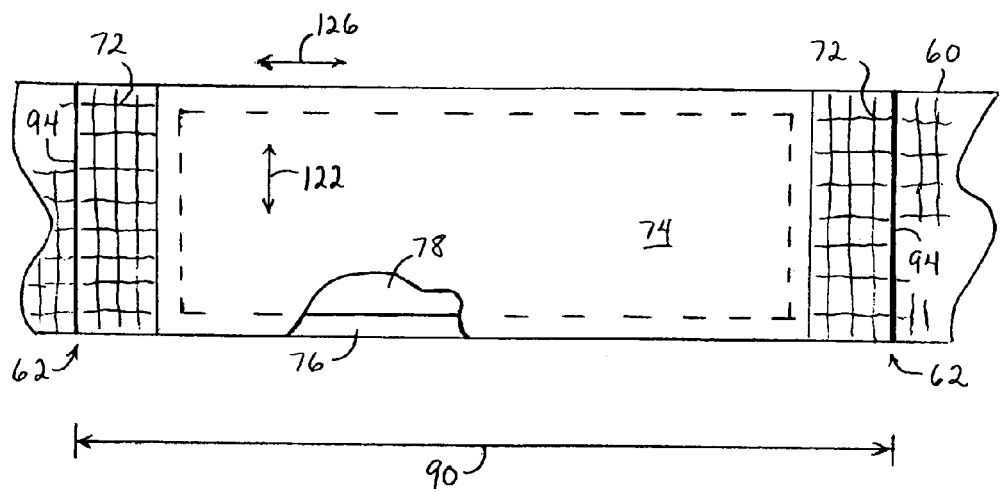
FIG. 2 shows a representative, partially cut-away, plan view of a representative web-segment or article that can be produced with the method and apparatus of the invention.
Figure 2A:
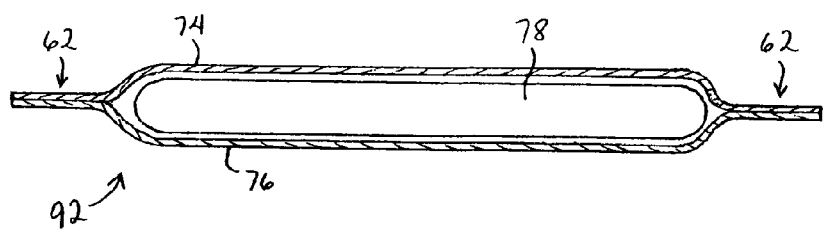
FIG. 2A shows a longitudinal, length-wise cross-section through a representative web-segment or article that can be produced with the method and apparatus of the invention.

With reference to FIGS. 1 through 2A, the method and apparatus can be configured to move the target, product web 60 at a selected speed along the machine-direction 126 of the method and apparatus. The product web can include an interconnected plurality of product segments 90, and appointed, processing target regions 62 can be located along the longitudinal, machine-direction 126 of the product web. The target regions can be irregularly or substantially regularly located along the longitudinal direction, as desired.

As representatively shown, an individual target region can include an appointed cutting region 94, and may also include an appointed bonding region 72. The bonding region can, for example, be configured to extend across selected bonding areas that are positioned along longitudinally-opposed sides of the cutting region. Accordingly, at least a portion of the bonding region can be configured to extend generally adjacent a transversely-extending, longitudinal border edge of an individual product 92 formed from the product web.

The product web 60 can be a multi-component composite web. As representatively shown, the composite product web can include a first component layer 74, and a second component layer 76. The composite structure of the product web can, for example, be produced from one or more individual webs of material which have been provided by conventional supply mechanisms. Such supplying systems are well known and available from commercial vendors. Additionally, the product web can include a plurality of individual articles 78, and in desired configurations, the articles can be absorbent personal care articles. The personal care articles can, for example, be configured as feminine care articles. The selected articles may also be configured to be reusable or disposable, as desired. In a particular arrangement, the composite web can be arranged to provide an interconnected plurality of packages, and each individual package can contain a selected personal care article.

The individual articles 78 can, for example, be intermittently positioned at spaced-apart locations along the longitudinal, machine-direction 126 of the product web 60, and can be operatively sandwiched and held between the first component layer 74 and the second component layer 76. The target, product web 60 can also include other web components or layers, as desired. The representatively shown first component layer 74 can extend substantially continuously along the longitudinal machine-direction 126 of the cutting method and apparatus. Similarly, the representatively shown second component layer 76 can extend substantially continuously along the longitudinal machine-direction 126 of the cutting method and apparatus.

Various known, conventional systems and techniques can be employed to position the individual articles 78 at spaced apart locations along the machine-direction 126 of the method and apparatus. Additionally, the selected second component layer 76 may be assembled with the first component layer 74 and the articles 78 by employing known, conventional mechanisms. As representatively shown, the second layer 76 and the articles 78 may be superposed onto the first layer 74. Other operative arrangements may optionally be employed, as desired.

For example, the first and second component layers 74, 76 may be provided by a single, unitary layer which has been folded or otherwise wrapped around the articles 78 to form a tube structure that operatively encloses the articles and extends longitudinally along the machine-direction 126. The tube structure may or may not include a construction seam that extends longitudinally along the machine-direction. An employed construction seam may be discontinuously bonded or substantially continuously bonded, as desired. Suitable wrapping or folding systems are well known and available from commercial vendors.

In the construction of the product web 60, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

In a particular arrangement, an operative adhesive can be employed to assemble together the various components of the desired product web 60. In a particular aspect, the product web 60 may include a selected pattern of adhesive that has been distributed between the first component layer 74 and the second component layer 76 of the product web. The adhesive pattern may be regular or irregular, and may be continuous or discontinuous, as desired. The adhesive can, for example, be distributed along at least a portion of the appointed target regions 62 of the product web.

Any operative adhesive applicator may be employed. Suitable applicators can include adhesive spray devices, adhesive coating devices, adhesive printing devices, or the like, as well as combinations there of. Conventional adhesive applicators are well known in the art, and available from commercial vendors. Any operative adhesive may be employed. Suitable adhesives can, for example, include hot melt adhesives, pressure-sensitive adhesives, solvent-based adhesives, pressure-sensitive adhesives, or the like as well as combinations thereof.

The employed adhesive applicator (not shown) can be configured to deposit a selected pattern of adhesive to join a plurality of individual articles 78 between the first component layer 74 and the second component layer 76. The selected articles 78 can be positioned at spaced-apart locations along the longitudinal, machine-direction of the method and apparatus and along the machine-direction of the composite product web 60. At least an operative portion of the selected adhesive pattern can be distributed along an appointed bonding region 72 of the product web 60, and can be distributed between the first component layer 74 and the second component layer 76. As representatively shown, an individual bonding region 72 can extend along and generally adjacent to at least a portion of a perimeter or border edge of an appointed individual product segment 90. Accordingly, at least a portion of the selected bonding region 72 can be positioned along and between the individual articles 78. Optionally, portions of the appointed bonding regions 72 may also be located laterally adjacent to each of the individual articles 78.

The first component layer 74 and the second component layer 76 may be constructed of any operative material, and the first and second layers 74, 76 may include the same or different materials, as desired. Optionally, the selected material of a selected component layer may be a composite material. The material of a selected component layer can, for example, include a woven fabric, a nonwoven fabric, a polymer film, or the like, as well as combinations thereof. Examples of a nonwoven fabric include, spunbond fabric, meltblown fabric, coform fabric, a carded web, a bonded-carded-web, or the like as well as combinations thereof. Other examples of suitable materials for constructing the selected component layer can include a net material or a foam material. For example, a closed cell polyolefin foam may be employed. The component layer material can, for example, include rayon, polyester, polypropylene, polyethylene, nylon, or other heat-bondable materials. The component layer material may also include other polyolefin such as copolymers of polypropylene and polyethylene, linear low-density polyethylene, aliphatic esters such as polylactic acid, and the like, as well as combinations thereof.

The first layer 74 and/or the second layer 76 may or may not be configured to be liquid-permeable. In a particular configuration, either or both of the component layers 74 and 76 may be configured to provide a desired level of liquid-impermeability. The selected component layer may, for example, include a polymer film laminated to a woven or nonwoven fabric. In another feature, the polymer film may be micro-embossed. A selected component layer can also be configured to operatively permit a desired passage of air and moisture vapor through the thickness of the component layer while effectively blocking the passage of liquids.

The first and/or second component layers 74, 76 may optionally be maintained in an operatively secured relation with the individual articles 78 by bonding all or a portion of their adjacent surfaces to one another. A variety of bonding mechanisms or systems known to one of skill in the art may be utilized to achieve any such secured relation. Examples of such mechanisms or systems can include, but are not limited to, the application of adhesives in a variety of patterns between the two adjoining surfaces, thermal bonding, sonic bonding, welding or the like, as well as combinations thereof.

The first and second component layers 74, 76 typically extend over and about each article 78 to at least partially enclose each article. Desirably, the first and second layers 74, 76 can be arranged to entirely, surround or enclose the article. The component layers can have peripheral margins which extend outwardly beyond the terminal, peripheral edges of the articles 78, and the extending margins can be operatively joined together to partially or entirely, surround or enclose each article. In a particular arrangement, the In desired arrangements, the layers 74 and 76 can be configured to form a package around each individual article, and the individual final product 92 can provide an individual packaged article.

As representatively shown, the cutting operation can operatively divide the product web 60 to provide a plurality of individual web segments 90 and a plurality of individual products 92. As the representatively shown, the individual product 92 can comprise a packaged article. As representatively shown, the cutting operation can employ a rotary cutter 28. The rotary cutter 28 can have any operative shape. As representatively shown, the rotary cutter 28 can be provided by a rotatable roll or wheel. The rotary cutter can be substantially circular or noncircular, as desired. Similarly, the rotary shaft member 30 can have any operative cross-sectional shape which may, for example, be circular or noncircular, as desired. Any conventional driving system may be employed to operatively rotate the cutter 28 and coordinate the operation of the cutter with the movement of the product web 60. Such systems are well known and available from commercial vendors.

With reference again to FIGS. 1, 1A and 3 through 5B, the outer peripheral surface 32 can extend along the axial and circumferential directions of the rotary cutter 28. As representatively shown, the axial-direction 22 of the rotary cutter 28 can be aligned substantially parallel to the local cross-direction 122 of the method and apparatus 20. In particular aspects, the radius of the rotary cutter 28 at its outer peripheral surface 32 can at least a minimum of about 5 cm. The radius of the rotary cutter can alternatively be at least about 8 cm, and can optionally be at least about 10 cm to provide improved performance. In other aspects, the radius of the rotary cutter can be up to a maximum of about 35 cm, or more. The radius of the rotary cutter can alternatively be up to about 30 cm, and can optionally be up to about 25 cm to provide improved effectiveness. The rotary cutter 28 can have any operative cross-sectional shape which may, for example, be circular or noncircular, as desired.

In a particular feature, the knife member 36 can be substantially fixedly attached to the rotary shaft member 30. In another feature, at least the circumferential location of the knife member 36 can be substantially fixedly positioned relative to the outer peripheral surface 32 of the rotary cutter 28. As a result, there is substantially no relative movement between the knife member 36 and the outer peripheral surface 32 of the rotary cutter 28 along the circumferential-direction 26 of the rotary cutter during the ordinary operation of the method and apparatus.

A plurality of knife members 36 can be circumferentially spaced-apart along the outer peripheral surface of the rotary cutter. The spacing between knife members can be regular or irregular, as desired. It should be readily appreciated that the circumferential spacing distance between the knife members, the diameter of rotary cutter at the knife members, and the rotational speed of the rotary cutter can be appropriately adjusted and configured to provide an operative cutting of the product web 60 at the appointed cutting regions 94 that operatively correspond to the desired, individual product segments 90, thereby helping to form the individual products 92.

The knife member 36 can be substantially straight and linear, nonlinear, curvilinear, or combinations thereof. Similarly, the cutting line provided by the knife member can be substantially straight and linear, nonlinear, curvilinear, or combinations thereof. In a particular aspect, the knife member 36 can be configured to provide a discontinuous cut or a substantially continuous cut, as observed along the axial-direction 22 of the shaft member 30.

The rotary cutter can be configured to provide either an incomplete separation of the cut article web 60, or a substantially complete separation of the cut article web, as desired. Where the cutting is incomplete, the desired final separation may be completed by applying a relatively low separating force to the article web. For example, the applied tearing force can be not more than a maximum of about 5 lb-force. Accordingly, the knife member 36 can be configured to cut through at least a portion of the thickness of article web 60, as observed along the radial-direction 24 of the rotary cutter 28. In a particular configuration the knife member 36 can be arranged to cut through at least a major portion of the thickness of article web. Another configuration of the method and apparatus can include a knife member 36 which is arranged to cut through substantially 100% of the thickness of article web 60.

With reference to FIGS. 3 through 5B, at least one peripheral bearing member 40, and desirably a cooperating pair of peripheral bearing members 40 can be located proximate to axially-opposed ends 38 of each knife member 36. With regard to a cooperating pair of axially-opposed peripheral bearing members 40 on the rotary cutter 28, the pair of bearing members can desirably have substantially the same configuration. Optionally, the opposing pair of peripheral bearing members can have different configurations.

In a particular feature, each peripheral bearing member 40 can be substantially rigidly affixed to the rotary cutter 28. In another feature, at least the circumferential location of the bearing member 40 can be substantially fixedly positioned relative to the outer peripheral surface 32 of the rotary cutter 28. As a result, there is substantially no relative movement between the peripheral bearing member 40 and the outer peripheral surface 32 of the rotary cutter 28 relative to the circumferential-direction 26 of the rotary cutter during the ordinary operation of the method and apparatus.

Particular arrangements of the method and apparatus can include an axial spacing distance 88 between an individual knife member 36 and each of its corresponding, cooperatively adjacent bearing members 40. In a desired feature, the axial spacing distance can be about 3 millimeters to provide improved performance.

In another feature, at least one of the peripheral bearing members 40 can extend discontinuously along the circumferential-direction 26 of the rotary cutter 28. In another feature, at least one of the peripheral bearing members 40 can extend substantially continuously along the circumferential-direction 26 of the rotary cutter. A further feature can include bearing members that have a substantially constant radial height away from the peripheral surface 32 of the rotary cutter. Alternatively, one or more of the bearing members can have a varying, non-constant radial height.

Figure 5:
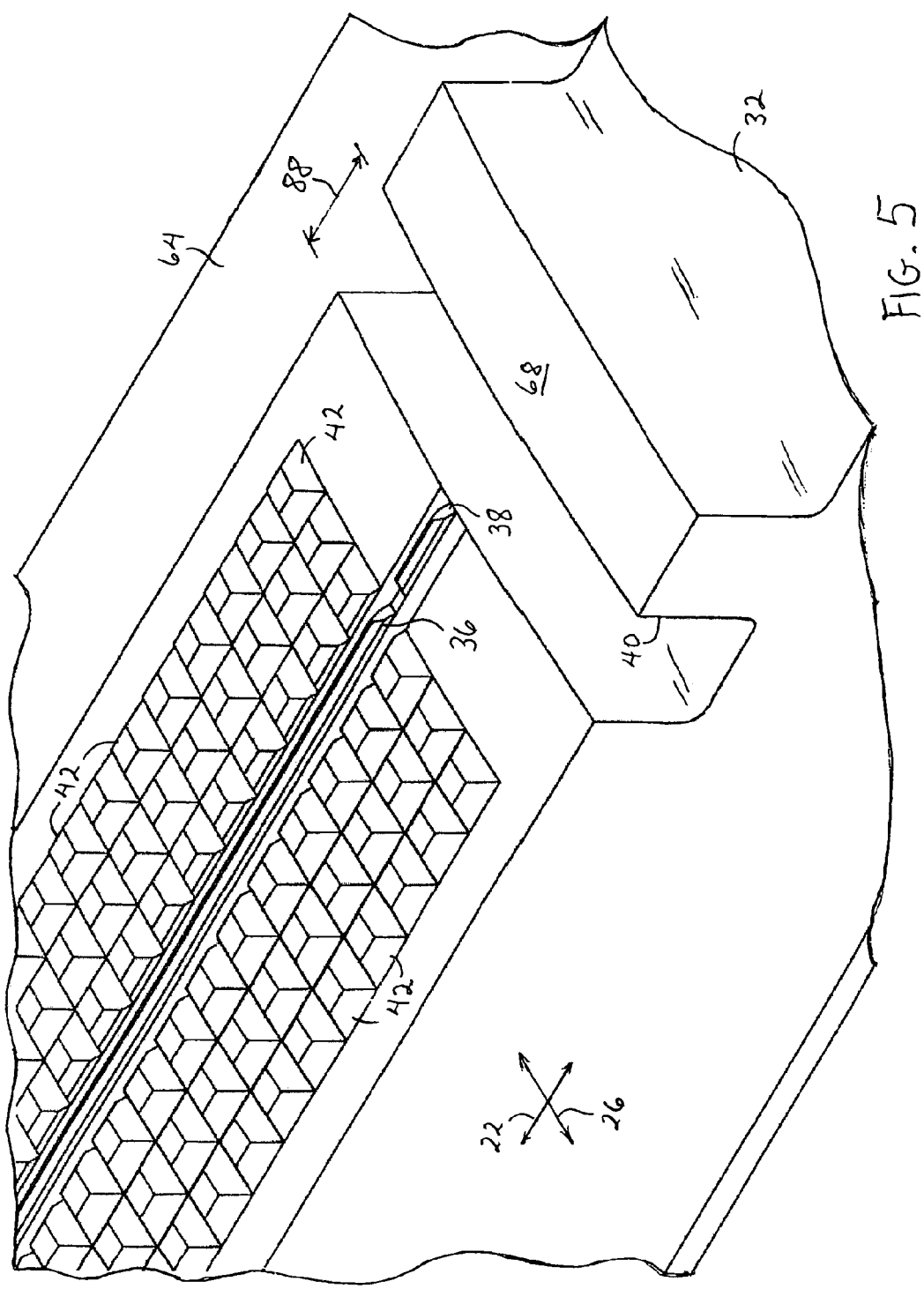
FIG. 5 shows an enlarged perspective view of a portion of a representative cutter insert member at one lateral end region.
Figure 5A:
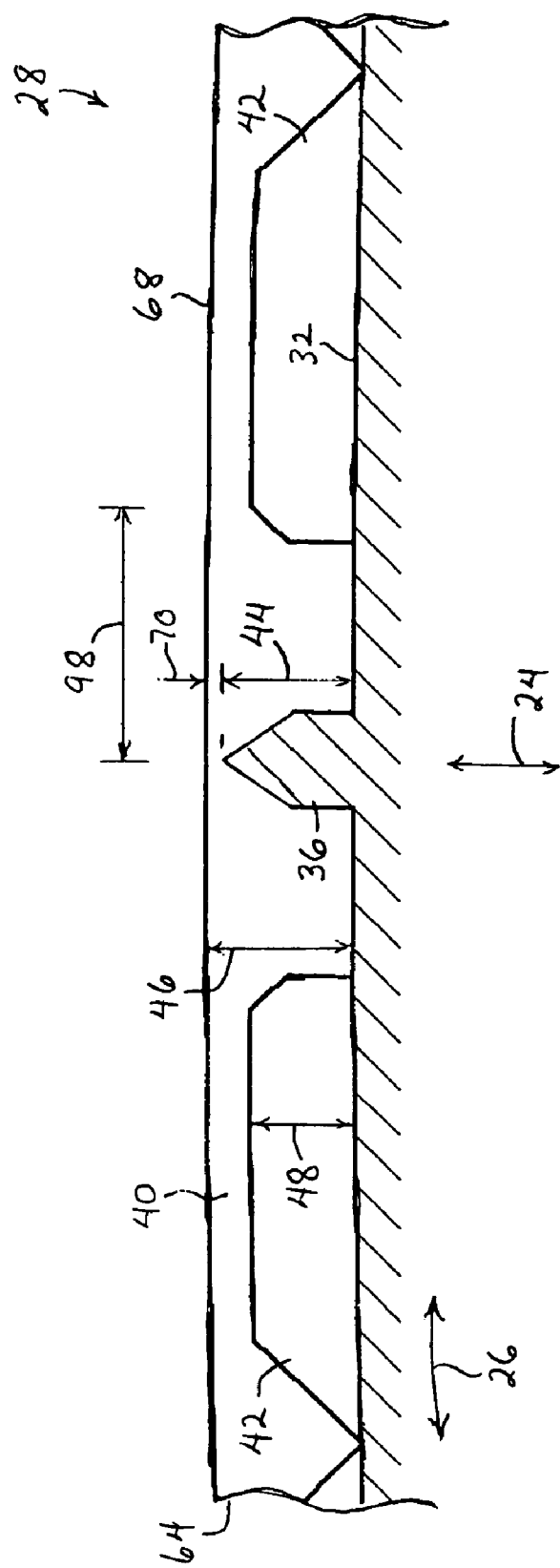
FIG. 5A shows an enlarged cross-sectional view of a representative cutter insert member. shows an enlarged cross-sectional view of a representative cutter insert member that has a cutter knife which extends radially beyond its cooperating bonding members.

With reference to FIGS. 5 through 5B, a radial-position distance of a radially-distal edge of the knife member 36 can be not more than a radial-position distance of a radially-outwardly facing, radially-distal bearing surface 68 of each of the peripheral bearing members 40. As representatively shown, the bearing surface 68 faces radially-outward from the rotary cutter 28. Accordingly, the radially-distal edge of the knife member 36 can have a selected radial height 44 which extends radially outward beyond the outer peripheral surface 32 of the rotary cutter, Similarly, the radially-distal bearing surface 68 of each peripheral bearing member 40 can have a radial height 46 which extends radially outward beyond the outer peripheral surface 32 of the rotary cutter. In a particular aspect, the radial height 44 of the knife edge can be less than the radial height 46 of its corresponding peripheral bearing member surface 68. As a result, the knife member and its associated bearing members can exhibit a selected spacing distance or height-differential 70 along the radial-direction 24. The height differential is determined with respect to that portion of the peripheral bearing member 40 that has a circumferential position that operatively matches and coincides with the circumferential position of the corresponding distal knife edge of the knife member 36 with which the peripheral bearing member 40 cooperates. Accordingly, the knife member 36 and its corresponding peripheral bearing members 40 can be cooperatively configured to provide a selected, radial height-differential 70 between the radially-distal edge of the knife member 36 and the cooperating radially-distal bearing surface 68 of each corresponding bearing member 40.

In a particular feature, the height-differential 70 can be configured to compensate for or accommodate a radial deflection that can occur when the peripheral bearing members 40 contact a cooperating anvil member 50. The height-differential 70 can be selectively configured so that the method and apparatus can substantially prevent an excessive contact between the knife member 36 and the anvil member 50. In desired arrangements, the height-differential 70 can be configured to provide an approximately zero distance between the distal, cutting edge of the knife member 36 and the cooperating outer surface of the anvil member 50 during the actual cutting operation. The radial height-differential 70 between the radial height 44 of the knife member 36 and the radial height 46 of the distal bearing surface 68 of the bearing member can be up to about 0.005 mm. The height-differential 70 can alternatively be up to about 0.01 mm, and can optionally be within the range of about 0.015 mm to provide a desired combination of reliable cutting and reduced maintenance of the knife member.

Figure 3:
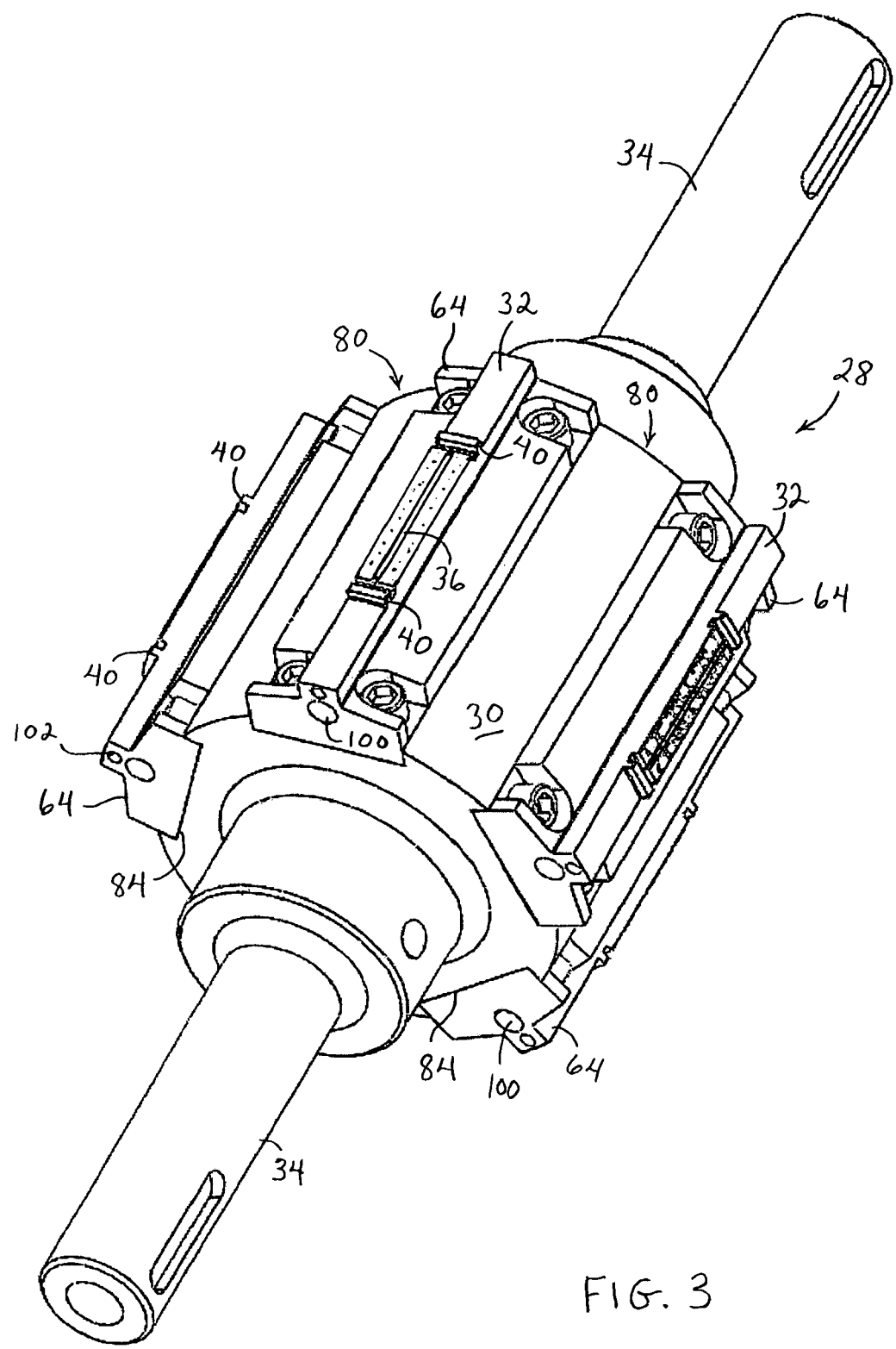
FIG. 3 shows a perspective view of a representative rotary cutter that can be employed with the present invention.

As representatively shown in FIGS. 1 and 3, the rotary cutter 28 can include relieved or recessed sections 80 of the rotary cutter to accommodate the passage of the product web through the nip region 56, particularly when the product web has a non-uniform, variable thickness. As representatively shown, the rotary cutter 28 has a smaller radial dimension at the locations of the recessed sections 80. The thicker portions of the product web 60 that contain an individual article 78 can be positioned in a recessed section 80 while the target regions of the product web are cut or bonded.

With reference to FIGS. 3 and 4 through 5B, the cutting method and apparatus can further include at least one crimping or other bonding member 42 which is operatively connected and joined to the rotary shaft member 30. Each bonding member can be located proximate a corresponding, cooperating knife member 36 and positioned circumferentially adjacent the knife member. In a desired configuration, the cutting method and apparatus 20 can further include at least a cooperating pair of bonding members 42 which are joined to the rotary shaft member 30. The cooperating pair of bonding members 42 can be located proximate the knife member 36 and positioned circumferentially adjacent to circumferentially-opposed sides of the knife member 36.

The bonding members 42 can be configured to operatively produce a securement seal or at appointed target regions 62 of the moving article web 60, particularly the appointed bonding regions 72. In a desired aspect, the bonding member 42 can be configured to operatively crimp and seal appointed target regions 62 of the moving article web 60. Each bonding member 42 can, for example, include a plurality of bonding protrusions which are distributed in a preselected pattern. The pattern can be regular or irregular, as desired. The bonding member can be configured to provide any operative crimping pattern. Additionally, the bonding member can be configured to provide any operative sealing pattern. The bonding of the appointed target regions of the moving web 60 can be configured to operatively hold and bond together the first and second layers 74, 76 at the target regions 62. Accordingly, the bonding members 42 can operatively close the longitudinal end portions of the final, individual products 92.

The method and apparatus can include a selected circumferential spacing distance 98 between each knife member 36 and each of its corresponding, cooperatively adjacent bonding members 42. In particular aspects, the circumferential spacing distance can be at least a minimum of about 0.3 mm. The circumferential spacing distance can alternatively be at least about 0.5 mm, and can optionally be at least about 0.7 mm to provide improved performance. In other aspects, the circumferential spacing distance can be up to a maximum of about 4 mm, or more. The circumferential spacing distance can alternatively be up to about 2 mm, and can optionally be up to about 1 mm to provide improved effectiveness. Accordingly, the bonding members 42 can operatively crimp and seal selected bonding regions 72 of the moving article web 60, and in combined, approximately simultaneous operation, the knife member 36 can operatively cut between an adjacent pair of the bonding regions.

Each knife member 36 and/or each bonding member 42 can be integrally and unitarily formed with the rotary shaft member 30. In a desired feature, the knife member 36 and/or bonding member 42 can be incorporated into a separately provided, insert component or member 64 that is subsequently attached and operatively affixed to the rotary shaft member 30.

As representatively shown in FIGS. 1A and 3, a selected array of at least one cutter insert member 64, and desirably a plurality of cutter insert members may be arranged and distributed along the outer peripheral rim of the rotary cutter 28. The selected array of cutter insert members can be operatively distributed along the axial dimension and/or circumferential dimension of the rotary cutter, as desired. Additionally, the plurality of cutter insert members 64 can be located at predetermined, spaced-apart locations along the circumferential direction 26 of the rotary cutter 28, and the cutter inserts 64 can be irregularly spaced or substantially equally spaced along the circumferential direction of the rotary cutter. Typically, the circumferential spacing distance between a sequential pair of knife members can equal or substantially correspond to the length of an individual product segment 90 of the product web 60 (e.g. FIG. 2). As representatively shown, the cutter members 64 can be distributed and operatively secured along the outer periphery of the rotary shaft member 30. Any operative number of cutter insert members 64 can be distributed along the outer circumference of the rotary cutter. In particular arrangements, for example, the number of distributed cutter members can be within the range of about 1–10. In a desired arrangement, the rotary cutter 28 can include an array of five cutter members 64 that are substantially evenly spaced along the peripheral circumference of the rotary shaft 30.

With regard to an individual cutter insert member 64, the cutter insert can provide a corresponding section of the outer peripheral surface 32 of the rotary cutter 28, and a corresponding knife member 36 can be substantially fixedly joined and attached to the cutter insert. Additionally, the cutter insert member 64 can include at least one peripheral bearing member 40, and can desirably include a cooperating pair of bearing members positioned adjacent the axially-opposed end regions of the knife member 36. At least one bonding member 42 can be located on the cutter insert 64, and desirably a cooperating pair of bonding members can be positioned adjacent the circumferentially-opposed sides of the knife member 36. The cutter insert members 64 can have any operative shape. As representatively shown, the individual cutter insert members 64 can have a generally rectangular shape with its longer dimension generally aligned along the axial-direction 22.

The rotary cutter, particularly the rotary shaft member 30, can include a mechanism for operatively holding each of the cutter inserts 64 in a predetermined, substantially fixed, circumferential location on the rotary cutter. In a desired configuration, the rotary shaft member 30 can include a system of mounting slots 84 formed into the shaft member 30. As representatively shown, the cutter slots 84 can have a length which is generally aligned along the axial-direction 22 of the rotary cutter, and can have a depth formed radially into the shaft member. Optionally, the length of the cutter slot can be non-aligned with the axial-direction 22 of the shaft member 30. The size and shape of the cutter slot is configured to operatively accommodate the placement of a corresponding cutter insert member 64 in the cutter slot. Any operable system of well known conventional attachments, such as welds or a system of threaded bolts, can be employed to affix the cutter inserts 64 to the shaft member 30. Accordingly, the cutter inserts 64 may or may not be removable and replaceable with respect to the rotary shaft member 30. Removable cutter inserts can help facilitate a more efficient maintenance and repair of the rotary cutter.

In alternative arrangements, the cutter insert member 64 and the rotary shaft 30 may optionally be configured to allow a predetermined amount of resilient displacement or movement along the radial-direction 24. As a result, the cutter insert 64 can selectively retract radially inward upon the application of a selected level of force, and can re-extend radially outward and return to substantially its original radial position when the applied force is removed.

Figure 6:
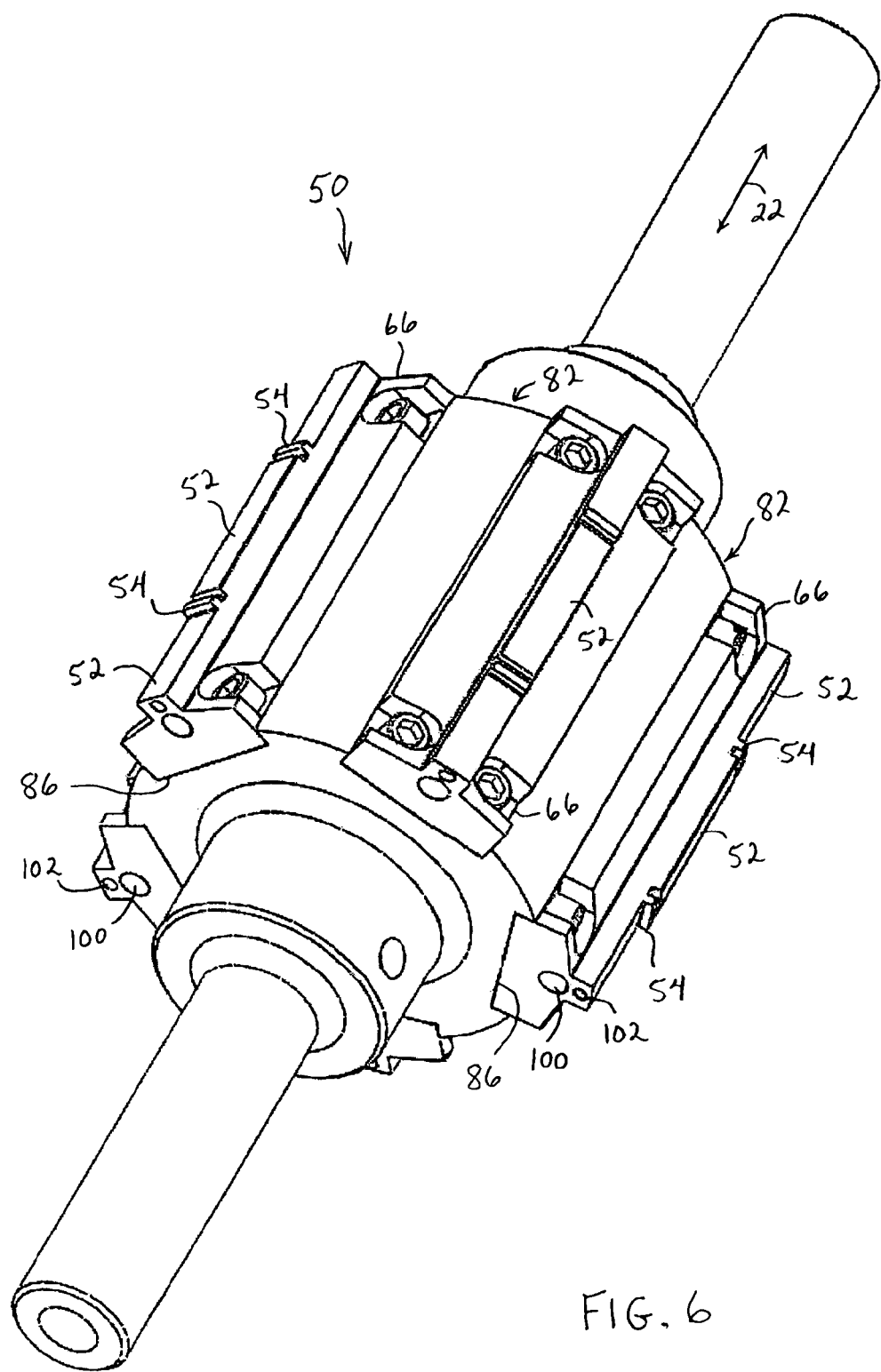
FIG. 6 shows a perspective view of a representative rotary anvil that can be employed with the present invention.
Figure 7:
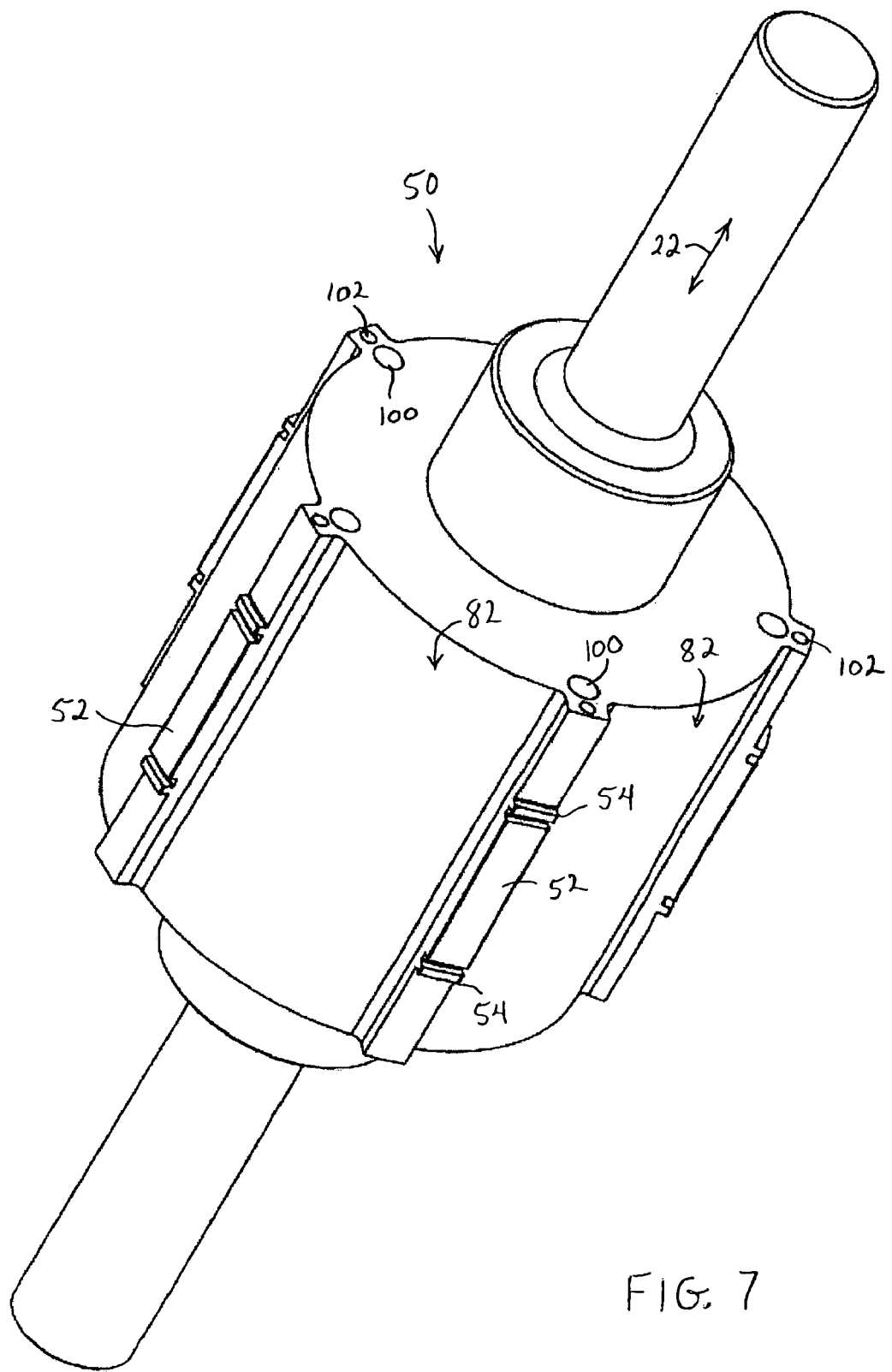
FIG. 7 shows a perspective view of a representative, alternative rotary anvil that can be employed with the present invention.

The cutting method and apparatus can further include a rotary anvil 50 which is located cooperatively adjacent the rotary cutter 28 to provide a nip region 56 between the rotary anvil 50 and the rotary cutter 28. In a particular arrangement, the outer peripheral surface 52 of the anvil 50 can be substantially smooth. With reference to FIG. 1A and FIGS. 6 through 7, the rotary anvil 50 can optionally include at least one pair of axially spaced-apart, outer peripheral bearing elements 54 which are operatively joined to the rotary anvil 50. Each peripheral bearing element 54 can extends circumferentially about the anvil 50, and may extend radially outward from an outer peripheral surface 52 of the anvil 50. Each peripheral bearing element 54 can be configured to cooperatively contact or otherwise engage a corresponding peripheral bearing member 40 of the rotary cutter 28. In a particular arrangement, each peripheral bearing element 54 can be substantially rigidly affixed to the rotary anvil 50.

The rotary anvil 50 can also include recessed, relieved sections 82 to accommodate the passage of the product web 60 through the nip region 56 when the product web has a non-uniform, variable thickness. Accordingly, the rotary anvil 50 can have a smaller radial dimension at the locations of the recessed sections 82. The method and apparatus can be configured to have the recessed sections 80 of the rotary cutter 28 substantially coincide with the recessed sections 82 of the anvil 50 during the operation of the method and apparatus.

The rotary anvil 50 can optionally include at least one anvil insert member 66 (e.g. FIG. 6), and can desirably include a plurality of anvil insert members 66 that are located at selected, spaced-apart locations along the circumferential direction 26 of the rotary anvil. The anvil insert members can be irregularly spaced or substantially equally spaced along the circumferential direction of the rotary anvil 50 The rotary anvil 50 can also include a mechanism for operatively holding each anvil insert 66 in a desired fixed position on the rotary anvil. In a desired configuration, the rotary anvil 50 can include a system of slots 86 formed into the anvil. As representatively shown the anvil slots 86 can have a length which is generally aligned along the axial-direction 22 of the rotary anvil, and can have a depth formed radially into the anvil member. Optionally, the length of the anvil slot 86 can be non-aligned with the axial-direction 22 of the rotary anvil. The size and shape of the anvil slot is configured to operatively accommodate the placement of a corresponding anvil insert member 66 in the anvil slot. Any operable system of well known conventional attachments, such as welds or a system of threaded bolts, can be employed to affix the anvil inserts 66 to the anvil 50. Accordingly, the anvil inserts 66 may or may not be removable and replaceable with respect to the anvil member 50. Removable anvil inserts can help facilitate a more efficient maintenance and repair of the rotary anvil. In other arrangements, the anvil can be configured with a substantially unitary structure (e.g. FIG. 7), and the desired, operative anvil components may be cast, machined or otherwise formed into a substantially one-piece structure.

With reference to FIGS. 1 and 1A, the method and apparatus 20 can further include a forcing mechanism (not shown) which can resiliently or otherwise operatively urge the rotary cutter 28 against the rotary anvil 50. The forcing mechanism can be provided by any operative technique or system. Such conventional techniques and systems are well known and are available from commercial vendors. Examples of a suitable forcing mechanism can include a pneumatic actuator system, a hydraulic actuator system, springs, weights, magnetic actuator systems, electromagnetic actuator systems or the like, as well as combinations thereof. The forcing mechanism is configured to generate sufficient force to provide an operative engagement between the peripheral bearing members 40 and the anvil member 50.

Any operative drive mechanism (not shown) can be configured to rotate the rotary cutter 28 and the rotary anvil 50. Such conventional drive mechanisms are well known and are available from commercial vendors. A suitable drive mechanism can, for example, include a fuel-powered engine, an electric motor, a pneumatic motor, a hydraulic motor, a turbine powered motor, or the like, as well as combinations thereof.

In the various arrangements of the method and apparatus of the invention, the rotary cutter 28 can be configured and rotated to provide a rotary-cutter, peripheral speed at the cutter knife member 36. In a particular aspect, the peripheral speed can be at least a minimum of about 45 cm/sec (centimeters per second). The rotary-cutter surface speed can alternatively be at least about 60 cm/sec, and can optionally be at least about 80 cm/sec to provide improved performance. Desired configurations can provide a peripheral speed of at least about 85 cm/sec. In other aspects, the rotary-cutter surface speed can be up to a maximum of about 500 cm/sec, or more. The rotary-cutter surface speed can alternatively be up to about 300 cm/sec, and can optionally be up to about 200 cm/sec to provide improved efficiency. It has been found that at high rotary cutter speeds there can be an excessive wear of the knife member and excessive maintenance requirements. By employing the various configurations and features of the invention, the method and apparatus can more reliably cut a product web at high speeds while substantially avoiding any excessive breakage of the product web.

The cutting and bonding systems of the invention can be constructed with any suitable material, such as steel, metal, metal composite, nonmetal composite material, synthetic polymer material or the like, as well as combinations thereof. Suitable materials with sufficient strength, toughness and durability are well known and available from commercial vendors. The rotary cutter 28 and the rotary anvil 50 can be operatively mounted in any suitable support system. As representatively shown, the rotary shaft member 30 can include a support axle 34 for operatively mounting the rotary cutter 28.

Figure 4:
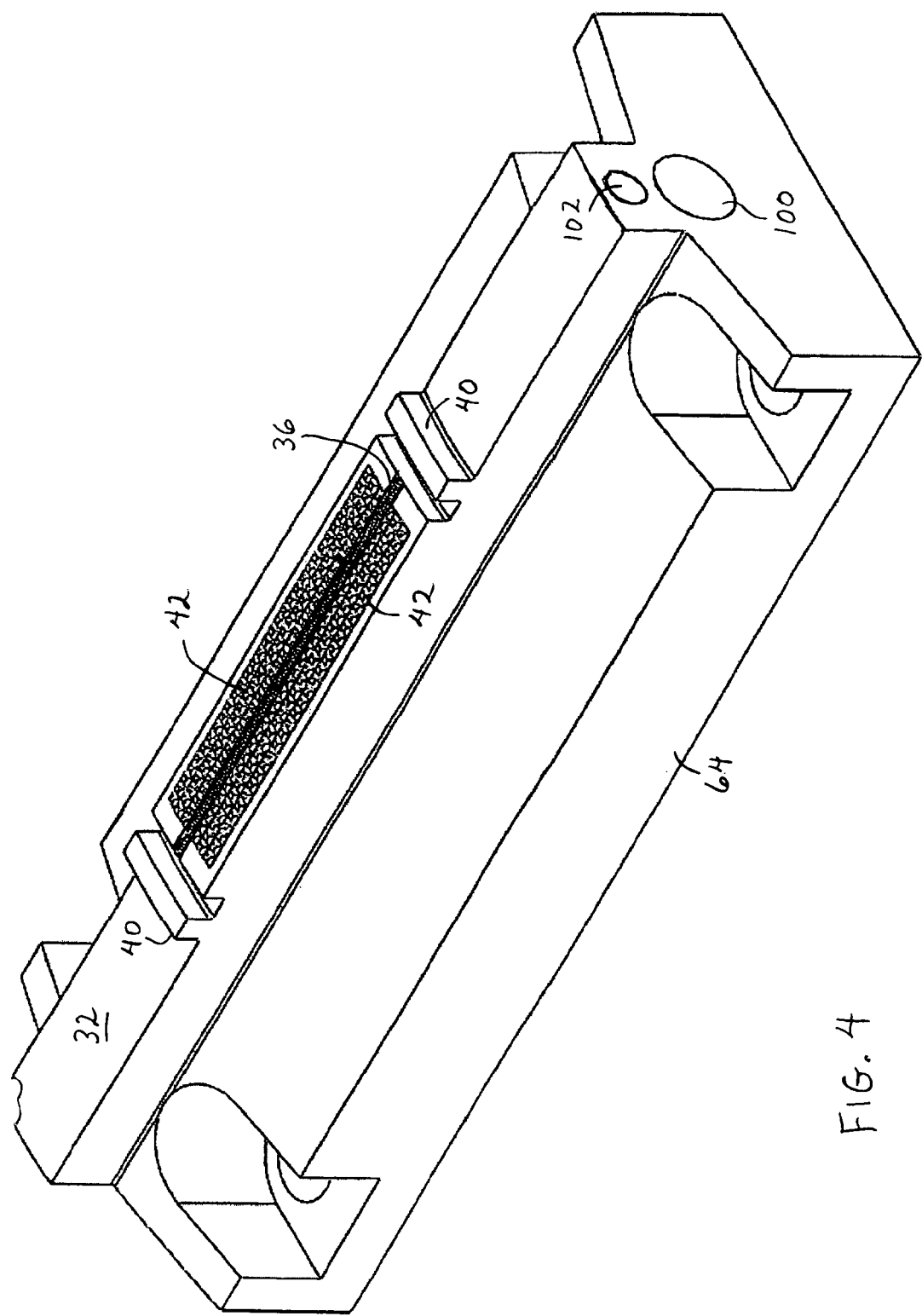
FIG. 4 shows a perspective view of a representative cutter insert member that be employed in the rotary cutter representatively shown in FIG. 3.
Figure 4A:
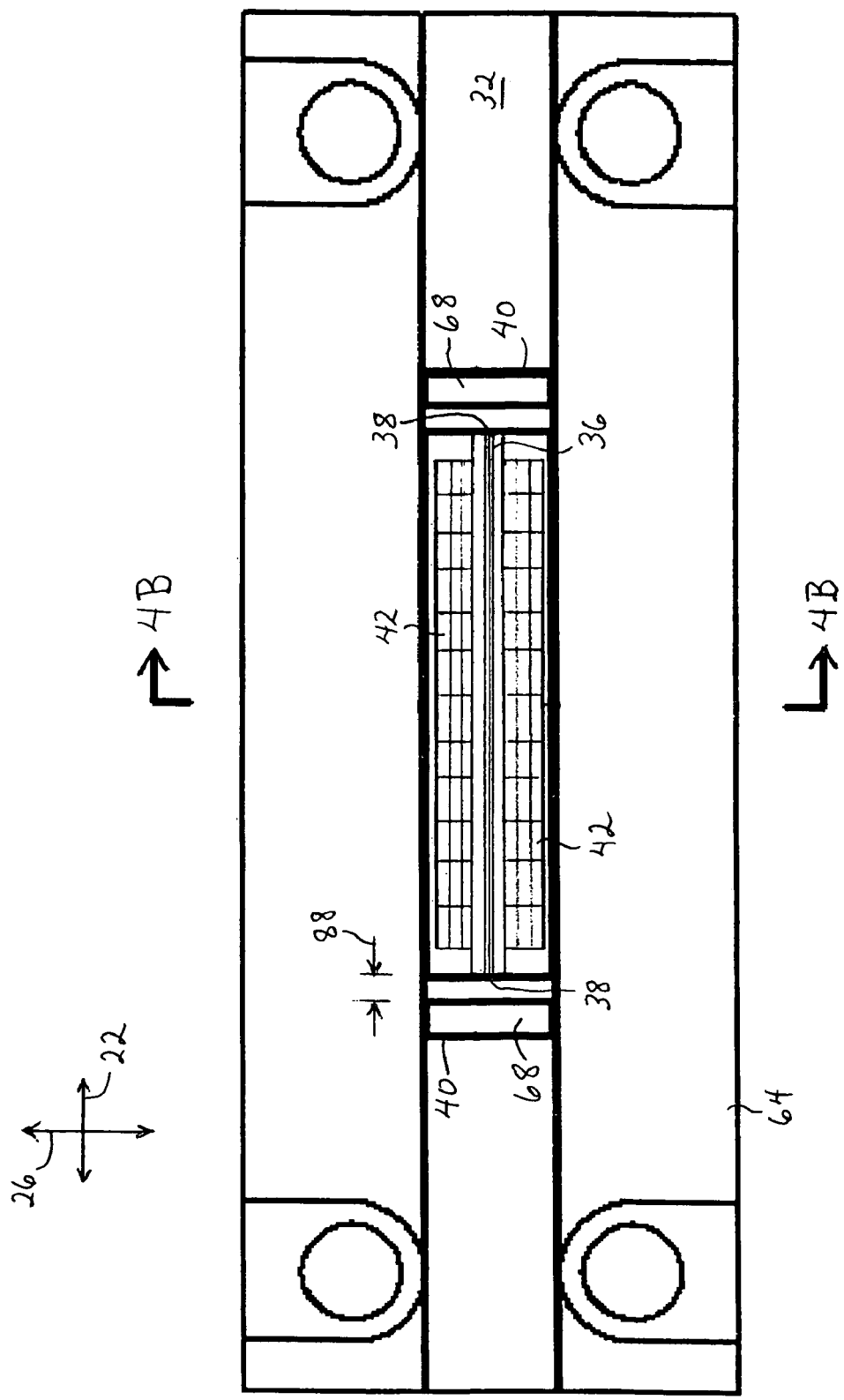
FIG. 4A shows a schematic top plan view of a representative cutter insert member.
Figure 4B:
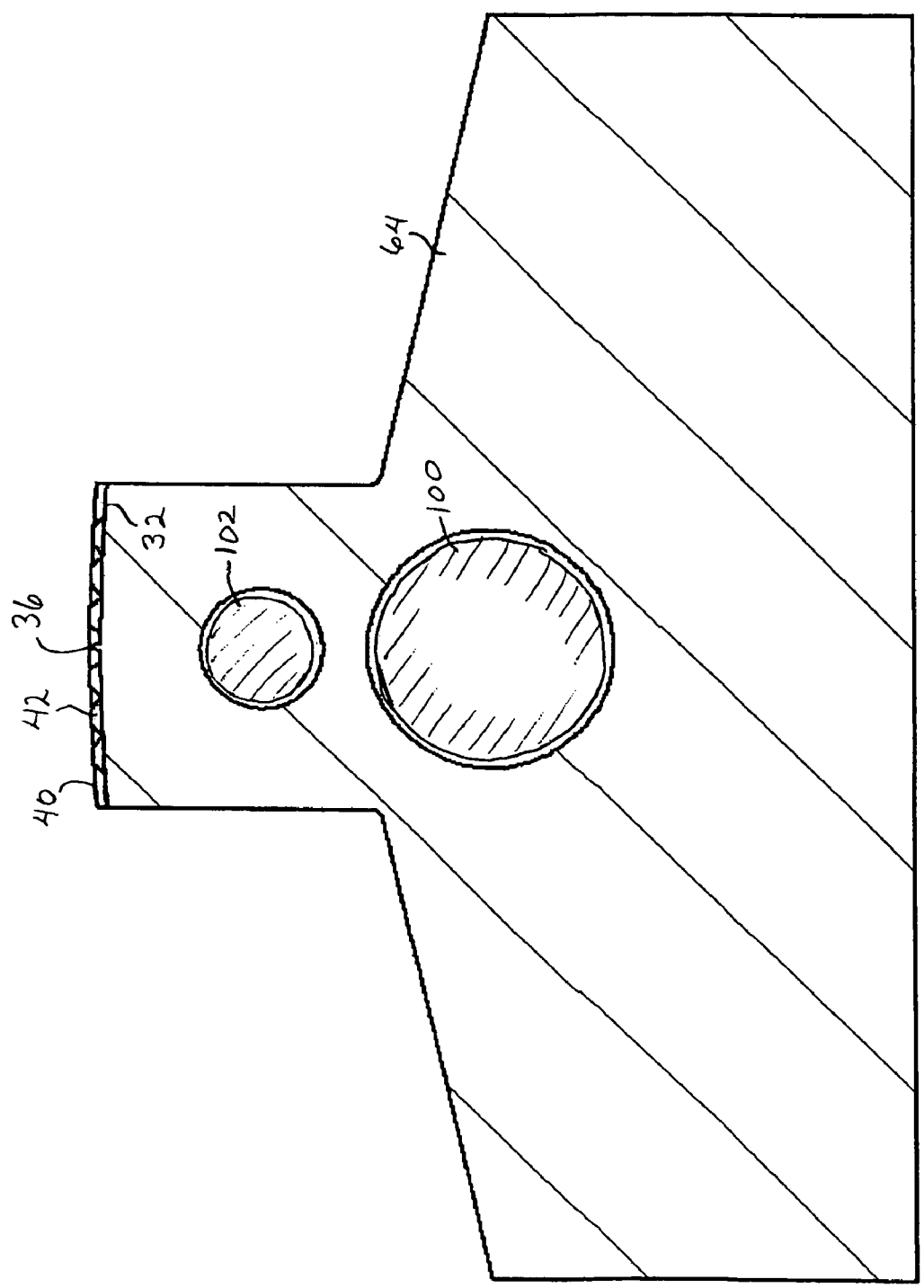
FIG. 4B shows a cross-sectional view of a representative cutter insert member.

In a further aspect, the rotary cutter 28 and/or anvil 50 can be heated or unheated, as desired. With reference to FIGS. 4, 4B and 6, an operative system of one or more heating elements 100 can be operatively incorporated into the rotary cutter 28 and/or the rotary anvil 50. Additionally, the heating system can include one or more temperature sensors 102. As representatively shown, a heating element and cooperating temperature sensor can be positioned operatively proximate the location each knife member 36, and in desired configurations can be included in each insert member 64 of the rotary cutter 28. In a like manner, individual heating elements and cooperating temperature sensors can be positioned operatively proximate a plurality of operating-surface portions of the rotary anvil 50 (e.g. FIG. 7), and in desired configurations can be included in each insert member 66 of the rotary anvil 50 (e.g. FIG. 6). It should be readily appreciated that the method and apparatus can also include a cooperating control system to provide and maintain a desired operating temperature. Any operative heating system may be employed. Such systems may be electric or non-electric, and are well known and available from commercial vendors. For example, suitable heating elements and electric heating systems may be obtained from Watlow Electric Manufacturing Company, a business having offices located in St. Louis, Mo., U.S.A.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A cutting apparatus comprising a rotary cutter having an axial-direction, a radial-direction and a circumferential-direction; said rotary cutter having an outer peripheral surface and including
   a rotary shaft member;
   at least one knife member joined to said shaft member, at least a portion of said knife member extending axially along said shaft member and extending radially outward from said shaft member, and at least one peripheral bearing member joined to said shaft member, at least an operative portion of said peripheral bearing member extending radially outward from said shaft member and extending circumferentially about said shaft member;

wherein said rotary cutter further includes at least one cutter insert member that is joined to said rotary shaft member;

said cutter insert member provides a section of said peripheral surface of the rotary cutter;

said at least one knife member is substantial fixedly attached to said at least one cutter insert member;

said at least one peripheral bearing member is joined to said at least one cutter insert member; and a circumferential location of said at least one cutter insert is substantiall fixed on said rotary cutter.

2. A cutting apparatus as recited in claim 1, wherein a pair of axially spaced-apart, peripheral bearing members are joined to said shaft member, at least an operative portion of each peripheral bearing member extending radially outward from said shaft member and extending circumferentially about said shaft member.

3. A cutting apparatus as recited in claim 1, wherein said knife member is substantially fixedly attached to said shaft member.

4. A cutting apparatus as recited in claim 1, wherein a plurality of said knife members are affixed to said shaft member and circumferentially spaced-apart along said outer peripheral surface of said shaft member.

5. A cutting apparatus as recited in claim 1, wherein said peripheral bearing members are located proximate axially-opposed ends of said knife member.

6. cutting apparatus as recited in claim 1, wherein a radial-position distance of a radially-distal edge of said knife member is not more than a radial-position distance of a radially-distal bearing surface of said peripheral bearing members.

7. A cutting apparatus as recited in claim 6, wherein said knife member and said peripheral bearing members are cooperatively configured to provide a selected radial height-differential between the radially-distal edge of said knife member and the radially-distal bearing surface of said bearing members.

8. A cutting apparatus as recited in claim 1, further including at least one crimping member which is joined to said shaft member and is located proximate said knife member and positioned circumferentially adjacent said knife member.

9. A cutting apparatus as recited in claim 1, further including at least a cooperating pair of crimping members which are joined to said shaft member, and are located proximate said knife member and positioned generally adjacent to circumferentially opposed sides of said knife member.

10. A cutting apparatus as recited in claim 9, wherein said crimping members are configured to produce a securement seal.

11. A cutting apparatus as recited in claim 1, further comprising a rotary anvil located cooperatively adjacent said rotary cutter to provide a nip region between said rotary anvil and said rotary cutter.

12. A cutting apparatus as recited in claim 11, wherein said rotary anvil includes at least a pair of axially spaced-apart, peripheral bearing elements joined to said rotary anvil, at least a portion of each peripheral bearing element extending radially outward from an outer peripheral surface of said anvil and extending circumferentially about said anvil;

each said peripheral bearing element of said anvil are configured to cooperatively engage a corresponding peripheral bearing member of said rotary cutter.

13. A cutting apparatus as recited in claim 1, wherein said peripheral bearing members are substantially rigidly affixed to said shaft member.

14. A cutting apparatus as recited in claim 1, further including a forcing mechanism which operatively urges said rotary cutter against said rotary anvil.

15. A cutting apparatus comprising a rotary cutter having an axial-direction, a radial-direction and a circumferential-direction, said rotary cutter having an outer peripheral surface and including a rotary shaft member;

at least one knife member joined to said shaft member, at least a portion of said knife member extending axially along said shaft member and extending radially outward from said shaft member; and at least one peripheral bearing member joined to said shaft member, at least an operative portion of said peripheral bearing member extending radially outward from said shaft member and extending circumferentially about said shaft member;

wherein at least one of said peripheral bearing members extends discontinuously along the circumferential-direction of said rotary cutter.

16. A cutting process, comprising rotating a rotary cutter which has an outer peripheral surface and includes a rotary shaft member;

wherein at least one knife member has been joined to said shaft member, at least a portion of said knife member extending axially along said shaft member and extending radially outward from said shaft member;

at least a pair of axially spaced-apart peripheral bearing members have been joined to said shaft member, at least a portion of each peripheral bearing member extending radially outward from said shaft member and extending circumferentially around said shaft member;

said rotary cutter further includes at least one cutter insert member that has been joined to said rotary shaft member;

said cutter insert member provides a section of said peripheral surface of the rotary cutter;

said at least one knife member has been substantially fixedly attached to said at least one cutter insert member;

said at least one peripheral bearing member has been joined to said at least one cutter insert member; and a circumferential location of said at least one cutter insert has been substantially fixed on said rotary cutter.

17. A process as recited in claim 16, wherein said knife member has been substantially fixedly attached to said shaft member.

18. A process as recited in claim 16, further including counter-rotating a rotary anvil which has been located cooperatively adjacent said rotary cutter to provide a nip region between said rotary anvil and said rotary cutter.

19. A process as recited in claim 16, wherein at least one crimping member has been joined to said shaft member and has been located proximate said knife member and positioned circumferentially adjacent said knife member.

20. A process as recited in claim 16, wherein a cooperating pair of crimping members have been joined to said shaft member, and have been located proximate said knife member and positioned generally adjacent to circumferentially opposed sides of said knife member.

21. A process as recited in claim 16, further including urging said rotary cutter against said rotary anvil with a selected, resilient force.

22. A process as recited in claim 16, further including rotating said rotary cutter to provide a cutter, peripheral surface speed which is at least a minimum of about 80 cm/sec.

23. A process as recited in claim 16, wherein at least one of said peripheral bearing members extends discontinuously along the circumferential-direction of said rotary cutter.

* * * * *